United States Patent [19]
Albright

[11] 3,978,167
[45] Aug. 31, 1976

[54] PENTAERYTHRITOL CYCLIC DIPHOSPHATES AND DIPHOSPHORAMIDATES

[75] Inventor: James A. Albright, Ann Arbor, Mich.

[73] Assignee: Michigan Chemical Corporation, Chicago, Ill.

[22] Filed: Sept. 26, 1975

[21] Appl. No.: 616,935

Related U.S. Application Data

[63] Continuation-in-part of Ser. No. 429,607, Jan. 2, 1974, abandoned.

[52] U.S. Cl. .................. 260/927 R; 260/45.7 PS; 260/45.7 P; 260/45.9 NP; 260/937; 260/960
[51] Int. Cl.² .................. C07F 9/09; C07F 9/165; C07F 9/24
[58] Field of Search ................. 260/927 R

[56] References Cited
UNITED STATES PATENTS

| | | | |
|---|---|---|---|
| 3,090,799 | 5/1963 | Wahl et al. | 260/927 R |
| 3,138,585 | 6/1964 | Rätz | 260/927 R X |
| 3,153,036 | 10/1964 | Merten et al. | 260/927 R X |

OTHER PUBLICATIONS
Pivawer et al., Index Chemicus, 28 (1968) 92699.

*Primary Examiner*—Richard L. Raymond
*Attorney, Agent, or Firm*—Robert M. Phipps

[57] ABSTRACT

Organophosphorus compounds of the formula

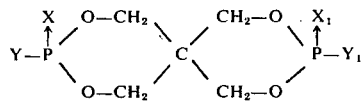

where X and $X_1$ are each oxygen or sulfur and Y and $Y_1$ are each monovalent halogenated oxyaliphatic or oxyalicyclic or

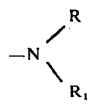

where R and $R_1$ are each hydrogen, monovalent hydrocarbon or halogenated monovalent hydrocarbon, are disclosed herein. The compounds are useful as flame-retardants for polymers.

22 Claims, No Drawings

PENTAERYTHRITOL CYCLIC DIPHOSPHATES AND DIPHOSPHORAMIDATES

This application is a continuation-in-part of applicant's prior copending application Ser. No. 429,607, filed Jan. 2, 1974, now abandoned.

BACKGROUND OF THE INVENTION

Compounds of the present invention can be characterized as pentaerythritol cyclic diphosphates and diphosphoramidates. The diphosphates are further characterized by halogen substitution on the oxyaliphatic or oxyalicyclic groups of the ester moiety. The diphosphoramidates can be optionally substituted with halogen atoms on the hydrocarbon substituents attached to the nitrogen atoms.

During the past several years, a large number of flame-retardants have been developed for use with an almost equally large number of flammable materials. Cellulosic materials such as paper and wood and polymeric materials such as synthetic fibers and bulkier plastic articles are just two examples of materials for which flame retardants have been developed. For any class of flammable materials, such as synthetic high polymers, those skilled in the art have long been aware that some flame-retardant additives are more effective in some polymers than they are in others. In fact, many flame-retardant additives which are highly effective in some polymer systems are virtually ineffective in other polymer systems. The mere fact, therefore, that most flame-retardants contain halogen and phosphorus atoms does not assure that any given halogenated or phosphorus-containing compound will impart useful flame-retardant characteristics to all or even to any polymeric systems. Furthermore, as those skilled in the art have improved the flame-retardancy of many polymeric materials, they have been simultaneously required to provide the necessary flame retardancy with a minimal effect upon other properties of the polymers such as their light stability, moldability and flexural, tensile and impact strengths. Balancing all of the foregoing considerations and thereby developing polymeric compositions with good flame-retardant characteristics as well as a satisfactory balance of other properties is, consequently, a task which has in the past and presently continues to require the exercise of a high degree of inventive skill.

SUMMARY OF THE INVENTION

Providing new compounds capable of imparting useful flame-retardant characteristics to synthetic polymer systems constitutes one of the principal objects of this invention. Additional objects will become apparent from the following detailed disclosure.

Compounds of the present invention have the generic formula

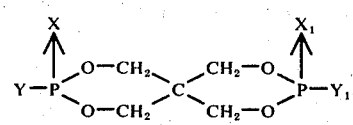

where X and $X_1$ are each oxygen or sulfur and Y and $Y_1$ are each monovalent halogenated oxyaliphatic or oxalicyclic or

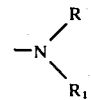

where R and $R_1$ are each hydrogen, monovalent hydrocarbon or halogenated monovalent hydrocarbon.

DESCRIPTION OF THE PREFERRED EMBODIMENTS

The compounds of the above formula include both the diphosphate esters and the diphosphoramidates of pentaerythritol. The compounds can also be generically described as 3,9-substituted-2,4,8,10-tetraoxa-3,9-phosphaspiro[5.5] undecane-3,9-dioxides or disulfides.

As indicated by the generic formula, the X groups attached to the phosphorus atoms can be either sulfur or oxygen. Oxygen is the preferred substituent for most compounds included herein, but the presence of thiophosphoryl groups, i.e.,

may be advantageous in some situations because of the difference in properties caused by their presence in place of the more customary phosphoryl groups.

The Y groups can be monovalent halogenated oxyaliphatic or oxyalicyclic groups or an amino group of the formula

where the R groups are hydrogen, monovalent hydrocarbon or halogenated monovalent hydrocarbon.

The oxyaliphatic and oxyalicyclic groups can be alkoxy, olefinicoxy and cycloalkoxy groups having any number of carbon atoms, preferably not more than about 12 carbon atoms and more preferably not more than about six carbon atoms. The halogen atoms present on the oxyaliphatic and oxyalicyclic groups include flourine, chlorine, bromine and iodine. Of the foregoing, chlorine and bromine are preferred. The number of halogen substituents is limited only by the number of sites on the aliphatic or alicyclic group available for their substitution. From a practical standpoint, the number of halogen atoms present on aliphatic or alicyclic groups having six or less carbon atoms will usually be from about one to about six. Examples of suitable halogenated monovalent aliphaticoxy or alicyclicoxy groups include bromoethoxy, dibromoethoxy, dibromopropoxy, dibromobutadieneoxy, tribromobutoxy, dichlorocyclophexoxy, dichlorobromocyclohexoxy, chlorodibromopropoxy, chlorodibromoneopentyloxy, difluorochloroethoxy, bromoiodopropoxy, difluorochlorohexoxy, dichlorohexabromoiodohexeneoxy, iodoethoxy, chloropentabromocyclohexoxy, fluorohexabromobutoxy, tetrafluorocyclobutoxy, diiodobuteneoxy, difluoroallyloxy, dibromodichlorohexeneoxy and the like.

When the Y groups are oxyaliphatic groups it is preferred that said groups each be

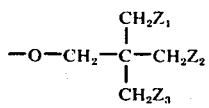

wherein $Z_1$ and $Z_2$ are independently selected from fluorine, chlorine, bromine, iodine, and hydrogen and $Z_3$ is selected from fluorine, chlorine, bromine, and iodine. Examples of suitable groups of the above neopentyloxy structure are listed in Table I, infra. Table I is for purposes of illustration only and is not to be construed as a limitation on the scope of this invention. The following is a partial listing of those preferred compounds which have the above neopentyloxy moiety: 3,9-bis(2,2-[dibromomethyl]-3-bromopropoxy)-2,4,8,10-tetraoxa-3,9-diphosphaspiro[5.5]undecane-3,9-dioxide, 3,9-bis(2,2-[dichloromethyl]-3-chloropropoxy)-2,4,8,10-tetraoxa-3,9-diphosphaspiro[5.5]undecane-3,9-dioxide, 3,9-bis(2,2-[dimethyl]-3-chloropropoxy)-2,4,8,10-tetraoxa-3,9-diphosphaspiro[5.5]undecane-3,9-dioxide, 3,9-bis(2,2-[dimethyl]-3-bromopropoxy)-2,4,8,10-tetraoxa-3,9-diphosphaspiro[5.5]undecane-3,9-dioxide, and 3,9-bis(2,2-[dibromomethyl]-3-chloropropoxy)-2,4,8,10-tetraoxa-3,9-diphosphaspiro[5.5]undecane-3,9-dioxide.

TABLE I

| Group | $Z_1$ | $Z_2$ | $Z_3$ |
|---|---|---|---|
| 1 | Br | Br | Br |
| 2 | Cl | Cl | Cl |
| 3 | H | H | Cl |
| 4 | H | H | Br |
| 5 | Br | Cl | Br |

The Y groups can also be amino groups of the formula

where R and $R_1$ are hydrogen, monovalent hydrocarbon or halogenated monovalent hydrocarbon.

The monovalent hydrocarbon groups can be aliphatic, naphthenic or aromatic and can be of any size, preferably not more than about 12 carbon atoms, and more preferably not more than about six carbon atoms. Preferred monovalent hydrocarbon groups are phenyl and alkyl groups having up to about six carbon atoms. The halogen atoms can be fluorine, chlorine, bromine or iodine, and preferably are chlorine or bromine. The number of halogen atoms present on the R groups is limited only by the sites on the R groups available for substitution. Preferably, each of the R groups will usually contain a maximum of about six halogens per R group, and more preferably about three halogens per R group.

The monovalent hydrocarbon groups are preferably aliphatic, halogenated aliphatic, aromatic, or halogenated aromatic groups containing not more than about 12 carbon atoms, said halogenated groups having up to about six halogen substituents per group.

Examples of suitable amino groups include amino, diethylamino, diphenylamino, propylamino, methylamino, dimethylamino, N-phenyl, N-methylamino, phenylamino, p-tolylamino, bromophenylamino, chloromethylamino, di-(chloroethyl)amino, N-ethyl, N-tribromocyclohexylamino, di-(tribormochloroethyl)amino, di-(dichlorobromoisopropyl)amino, butadienylamino, di(fluorocyclopentyl)amino and di-(diiodoethyl)amino.

All of the aforedescribed and aforementioned Y and $Y_1$ groups can be attached to the diphosphoryl or dithiophosphoryl pentaerythritol group, also characterized as 3,9-substituted-2,4,8,10-tetraoxa-3,9-diphosphaspiro[5.5]undecane-3,9-dioxide or disulfide. The numerical designations of the compounds of this invention can be ascertained by reference to the following formula where the members of the heterocyclic rings are numbered.

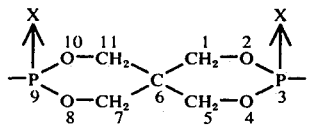

Two representative compounds are 3,9-bis(2,3-dibromopropoxy)-2,4,8,10-tetraoxa-3,9-diphosphaspiro[5.5]undecane-3,9-dioxide and 3,9-bis(N,N-diethylamino)-2,4,8,10-tetraoxa-3,9-diphosphaspiro[5.5]undecane-3,9-dioxide. Two additional representative compounds are the 3,9-disulfide analogs of the above two compounds. Additional 3,9-bis-substituted compounds, formed by placing the aforementioned halogenated oxyaliphatic and oxyalicyclic groups and the optionally halogenated substituted amino groups on the diphosphoryl and dithiophosphoryl pentaerythritol groups, constitute additional examples of compounds within the scope of this invention. The disulfide analogs of the foregoing compounds are further examples.

In addition to the 3,9-bis-substituted compounds, an ever larger number of 3,9-substituted compounds where the 3- and 9- substituents are different from each other are also included within the scope of this invention. The substituents can be varied to produce mixed diphosphate esters, mixed diphosphoramidates and combination phosphate - phosphoramidate compounds. Exemplary combinations of 3- and 9- substituents include dibromoethoxy and tribromochlorobutoxy; dibromopropoxy and dibromochloroneopentyloxy; diethylamino and dibromopropoxy; and unsubstituted amino and diiodoisopropoxy.

The compounds of the present invention are prepared by reacting a 3,9-dihalo-2,4,8,10-tetraoxa-3,9-diphosphaspiro[5.5]undecane-3,9-dioxide or disulfide with an alcohol or an amine to yield the appropriate diphosphate ester or diphosphoramidate. The equation for the reaction is:

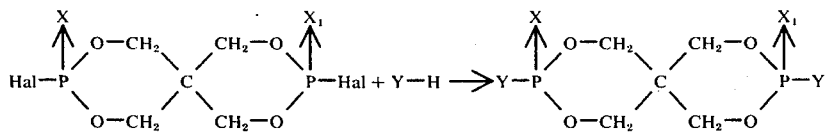

where Y has the meaning set forth above in the description of the compounds and where Hal indicates a halogen atom.

As an alternative reactant for the alcohol or amine, the metal salts of the alcohol or amine can be used. If it is desired that the two Y groups be different from each other, two different Y-H reactants should be employed. The reaction can be carried out by simply mixing the halophosphate and the alcohol or amine reactants together and heating the mixture gently for a period of time. The conditions of reaction will vary widely depending upon the reactants, but heating the reactants under gentle refluxing conditions for a period of time of up to 3 or 4 hours is acceptable for preparing many of the compounds of this invention. Catalytic quantities of a transition metal salt or oxide such as magnesium chloride, calcium oxide, calcium chloride, titanium chloride or vanadium acetate, or stoichiometric quantities of a weak organic base such as pyridine or triethylamine can be used to accelerate the completion of the reaction. The halophosphate starting reactant can be prepared by reacting pentaerythritol with phosphorus oxyhalide. The chlorophosphate is a preferred reactant and phosphorus oxychloride is therefore a preferred precursor of that reactant.

Also within the scope of this invention are pentaerythrotol cyclic diphosphoramidates wherein the Y groups are amino groups of the formula

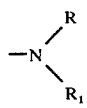

where R and $R_1$ are hydrogen, monovalent hydrocarbon, or halogenated monovalent hydrocarbon groups, but provided that when R and $R_1$ are both hydrogen and X and $X_1$ are both oxygen, Y must be different from $Y_1$. The monovalent hydrocarbon groups are preferably aliphatic, halogenated aliphatic, aromatic, or halogenated aromatic groups containing not more than about 12 carbon atoms, and more preferably, not more than about six carbon atoms, said halogenated groups having up to about six halogen substituents per group, and preferably up to about three halogen substituents per group. The halogen atoms can be fluorine, chlorine, bromine, or iodine, and preferably are chlorine or bromine. It is further preferred that when the Y groups are amino groups, that said Y groups be of the formula

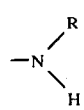

wherein R has been defined above.

Compounds of the present invention are useful as flame-retardants in polymeric compositions. Selected compounds may also exhibit pesticidal properties, making them useful both as agricultural chemicals and in the control of household pests.

The following examples are provided for the purpose of further illustration only and are not intended to be limitations on the disclosed invention. Unless otherwise specified, all temperatures are expressed in degrees centigrade; all weights are expressed in grams; and all volumes are expressed in millimeters.

EXAMPLE 1

A quantity of 29.7 grams of 3,9-dichloro-2,4,8,10-tetraoxa-3,9-diphosphaspiro[5.5]undecane-3,9-dioxide, 43.6 grams of 2,3-dibromopropanol and 0.1 gram of magnesium oxide were mixed together and heated to 110°C. to drive off the hydrogen chloride as it evolved. Hydrogen chloride evolution stopped after about two hours, at which time the reaction mixture was permitted to cool to room temperature. The resultant viscous product was washed with ammonium hydroxide at 60°C. and then with water. The light brown viscous liquid was dried under vacuum. Percent bromine calculated for 3,9-bis(2,3-dibromopropoxy)-2,4,8,10-tetraoxa-3,9-diphosphaspiro[5.5]undecane-3,9-dioxide is 48.5%. Percent bromine found by elemental analysis was 47.7%.

EXAMPLE 2

Dibromopentaerythritol cyclic chlorophosphite,

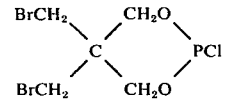

was prepared by reacting dibromopentaerythritol with a slight molar excess of phosphorus trichloride.

The above chlorophosphite, 380 grams, was then reacted with a slight molar excess of gaseous chlorine, 95 grams, in the presence of 200 ml. of methylene dichloride. An ice bath was used during the chlorine addition to hold the reaction temperature to 25° to 30°C. After the chlorine addition was complete, the methylene dichloride was evaporated, leaving the product, 2,2-di-(bromomethyl)-3-chloropropyl dichlorophosphate,

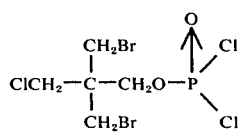

A quantity of 279 grams (0.7 mole) of the above dichlorophosphate was mixed with 47.7 grams (0.35 mole) of pentaerythritol in the presence of 300 ml. of toluene and 0.5 gram of magnesium oxide. The reaction mixture was heated to reflux temperature to remove hydrogen chloride. After about 12 hours at reflux temperature, the mixture was allowed to cool and was subjected to vacuum to remove additional hydrogen chloride. The white precipitate was filtered and washed once with ammonium hydroxide and twice with water, and then crystallized from methanol. The product was identified as 3,9-bis(2,2-di-bromomethyl-3-chloropropoxy)-2,4,8,10-tetraoxa-3,9-diphosphaspiro[5.5]undecane-3,9-dioxide. Melting point was 212°C. Calculated halogen content is Br 40.7%, Cl 8.93%; found Br 41.1%, Cl 9.12%.

EXAMPLE 3

To a suspension of 29.7 grams (0.1 mole) of 3,9-dichloro-2,4,8,10-tetraoxa-3,9-diphosphaspiro[5.5]undecane-3,9-dioxide in 250 ml. of benzene was added 30 grams of diethylamine in 50 ml. of benzene. The mixture was heated to reflux temperature for three hours and then filtered to remove the precipitated amine hydrochloride. Upon evaporation of the benzene, a clear oil remained which crystallized upon cooling, and was subsequently recrystallized from water. Melting point of the white crystalline product was 189.5° to 190.5°C. Calculated elemental analysis for 3,9-bis(N,N-diethylamino)-2,4,8,10-tetraoxa-3,9-diphosphaspiro[5.5]undecane-3,9-dioxide was C 42.2%; H 7.6%; N 7.6%. Found C 41.1%; H 7.5%; N 7.2%.

EXAMPLE 4

To 122 grams of the chlorophosphate of Example 3 in 800 ml. of toluene was added 146 grams of p-bromoaniline and 82 grams of triethylamine. The mixture was heated to 95°C for 4 hours and then allowed to cool. Two layers formed and the toluene was decanted. The product layer was washed with 800 ml. of water and then with boiling acetone to yield a white solid with a melting point of 276° to 278°C. Bromine content calculated for 3,9-bis-(N-p-bromophenyl)amino-2,4,8,10-tetraoxa-3,9-diphosphaspiro[5.5]undecane-3,9-dioxide was 28.2%. Bromine content found was 30.0%.

EXAMPLE 5

Preparation of 3,9-bis(2,2-[dimethyl] -3-chloropropoxy)-2,4,8,10-tetraoxa-3,9-diphosphaspiro[5.5]undecane-3,9-dioxide.

A quantity of 2,2-dimethyl-3-chloropropyl dichlorophosphate (748.2 gm; 3 moles) was dissolved in 800 ml. of toluene. To the above was added 209 gm (1.5 moles) of pentaerythritol and 3 gm of magnesium oxide. The solution was refluxed at 110°C. for 9 hours. The mixture was filtered leaving a white solid. This material was washed with 1 liter of acetone, followed by a wash with an aqueous ammonia solution having a pH of from about 8 to about 9. This solution was filtered and washed with 2 liters of water followed by a final acetone wash of 1 liter. The material was dried in a forced air oven at 105°C. for 3½ hours. About 442 gm of material was recovered giving a yield of about 63%. The melting point of the compound was determined to be 282° to 285°C.

EXAMPLE 6

Preparation of 3,9-bis(2,2-[dibromomethyl] -3-bromopropoxy)-2,4,8,10-tetraoxa-3,9-diphosphaspiro[5.5]undecane-3,9-dioxide.

A quantity of phosphoryl chloride (50 gm) and 0.4 gm of magnesium oxide were heated to 85°C. Tribromoneopentyl alcohol (300 gm; 0.924 moles) was added in increments over a 1.25 hour period. The reaction continued at a temperature of 85° C. for 6 hours. The excess phosphoryl chloride was distilled under an aspirator vacuum to a pot temperature of 130°C. The reaction was cooled to 100°C. and 0.462 mole (62.8 gm) of pentaerythritol and 300 ml of toluene were added. Additional toluene was added as needed. The system was refluxed for 6½ hours, cooled to room temperature, filtered, and dried at 100°C. in a vented oven.

The residue was washed with about 1 liter of water. An aqueous ammonia solution was added to give a pH of about 8. The residue was then washed with water and then with acetone and finally dried at 100°C. in air vented oven. Yield: 335 gm (83%); Melting point: 225°–228°C.

EXAMPLE 7

Preparation of 3,9-bis(2,2-[dichloromethyl] -3-chloropropoxy)-2,4,9,10-tetraoxa-3,9-diphosphaspiro[5.5]undecane-3,9-dioxide.

About 1 mole of 2,2-dichloromethyl-3-chloropropyl dichlorophosphate was placed into a 3 liter flask. To this was added 1 gm of magnesium oxide, 2 liters of toluene, and 0.5 mole of pentaerythritol. The reaction was stirred and heated at reflux until the acid number was less than 10. The toluene was stripped off and the solid portion was placed in an oven and dried without being washed. The product was ground up after having been dried for 4 hours at 110°C. and washed with a 50/50 acetone/water solution. The resulting product had a melting point of 197° to 200°C. and the melt remained clear until decomposition was reached at 270° to 280°C.

EXAMPLE 8

The following compounds were synthesized:

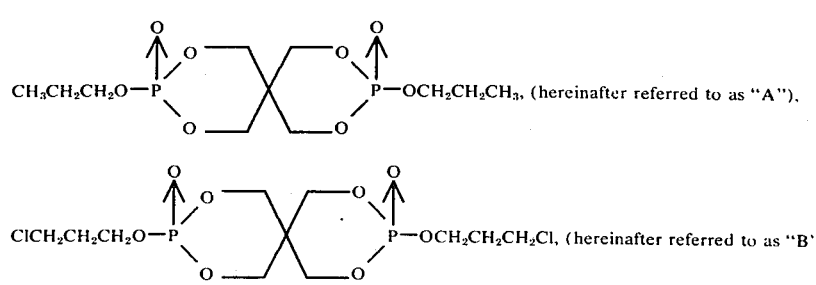

-continued

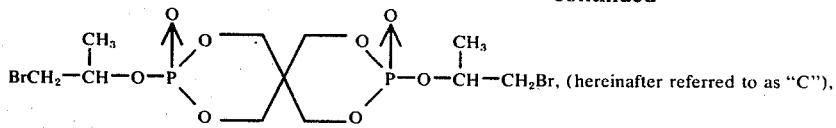
(hereinafter referred to as "C"),

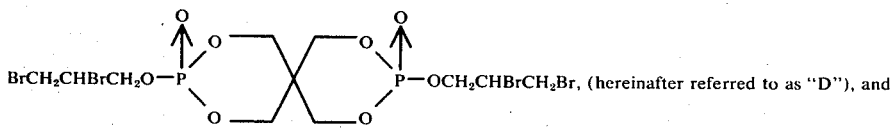
(hereinafter referred to as "D"), and

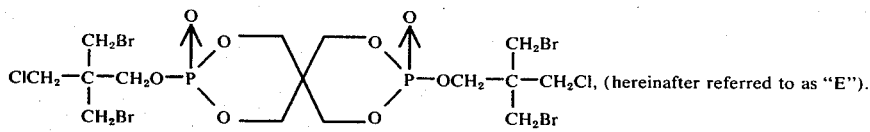
(hereinafter referred to as "E").

Compound (D) above was synthesized according to Example 1, supra. Compound (E) above was synthesized according to Example 2, supra. Compounds (A), (B), and (C) above were synthesized by the general method disclosed in Example 3 of U.S. Pat. No. 3,090,799 (hereinafter referred to as Wahl et al.) and said compounds were identified by nuclear magnetic resonance (NMR) spectroscopy and were found by said technique to have a purity of greater than 95%.

Compounds (A), (B), (C) and (D) above are representative of compound outside the invention as claimed herein but within the scope of Wahl et al. Compound (E) is representative of the pentaerythritol cyclic diphosphates of the presently claimed invention.

EXAMPLE 9

The hydrolytic stability of the above synthesized compounds of Example 8 were determined by the following procedure: A magnetically stirred emulsion containing 4 grams of Compounds (A), (B), (C), (D), or (E), above, 1 gram Emcol AM2-10C emulsifier (Emcol AM2-10C emulsifier is a mixture of free acid of phosphated nonionic plus nonionic; Emcol AM2-10C is a trademark of Witco Chemical Corporation, New York, N.Y.), and 45 grams of water was heated at 100°C. for 44 hours. The acid number of the emulsion was then determined by titration with a standard potassium hydroxide solution and the results are tabulated in Table II, infra.

TABLE II

| Compound | Hydrolytic Stability Tests Acid No. (mgKOH/g Sample) | Compound/E. × 100%[1] |
|---|---|---|
| A | 21.6 | 911 |
| B | 19.3 | 814 |
| C | 23.4 | 987 |
| D | 9.45 | 399 |

TABLE II-continued

| Compound | Hydrolytic Stability Tests Acid No. (mgKOH/g Sample) | Compound/E. × 100%[1] |
|---|---|---|
| E | 2.37 | — |

[1]Percent decrease in hydrolytic stability of prior art compound when compared to the pentaerythritol cyclic diphosphates of the presently claimed invention as represented by Compound E.

A compound's acid number is inversely proportional to the hydrolytic stability of that compound, i.e. the larger a compound's acid number, the poorer will be said compound's hydrolytic stability.

EXAMPLE 10

The thermal stability of compounds (A), (B), (C), (D), and (E), above, as well as 3,9-bis(2,2-[dimethyl]-3-chloropropoxy)-2,4,8.10-tetraoxa-3,9-diphosphaspiro[5.5]undecane-3,9-dioxide (prepared in Example 5, supra, and hereinafter referred to as F), 3,9-bis(2-2[dibromomethyl] -3-bromopropoxy)-2,4,8,10-tetraoxa-3,9-diphosphaspiro[5.5]undecane-3,9-dioxide (prepared in Example 6, supra, and hereinafter referred to as G), and 3,9-bis(2,2-[dichloromethyl] -3-chloropropoxy)-2,4,8,10-tetraoxa-3,9-diphosphaspiro[5.5]undecane-3,9-dioxide (prepared in Example 7, supra, and hereinafter referred to as H) was determined by the procedure set forth in Section 9-951, "Thermogravimetric Analyzer," of "Instruction Manual 990, Thermal Analyzer and Modules", E.I. Du Pont De Nemours and Co. (Inc), Instrument Products Division, Wilmington, Del. 19898. The results of the thermogravimetric analyses (TGA) of the eight compounds at several different weight losses are tabulated in Table III below:

TABLE III

| | TGA Results Temperature at which Weight Change Occurs, °C. | | | | | | | |
|---|---|---|---|---|---|---|---|---|
| Compound | A | B | C | D | E | F | G | H |
| Initial Weight Loss | 45 | 100 | 70 | 100 | 241 | 270 | 180 | 240 |
| 5% Weight Loss | 130 | 172 | 145 | 180 | 258 | 302 | 290 | 317 |
| 10% Weight Loss | 158 | 203 | 218 | 204 | 286 | 305 | 313 | 338 |
| 25% Weight Loss | 225 | 242 | 250 | 224 | 310 | 307 | 335 | 370 |
| 50% Weight Loss | 347 | 300 | 278 | 260 | 331 | 344 | 355 | 390 |

Table III clearly indicates that compounds (E), (F), (G), and (H) have unobviously superior thermal stability when compared to close prior art compounds.

The superior thermal and hydrolytic stability of the compounds with the scope of the invention as claimed has significant commercial implications. The superior hydrolytic stability of the compounds within the above narrow subgroup enables said compounds to be superior flame retardants when applied via an aqueous system because the surrounding aqueous environment would not cause said compounds to break apart as readily as would the close prior art compounds of Wahl et al.; for the same reasons, the compounds within the narrow subgroup are also superior flame retardants for incorporation into articles of manufacture which have a contemplated use wherein said articles would be subject to exposure to moisture.

The superior thermal stability of the compounds within the above narrow subgroup enables said compounds to be processed without significant weight losses at temperatures wherein close prior art compounds within Wahl et al. exhibit substantial weight losses such that said prior art compounds are not commercially capable of being used. For example, polypropylene is typically processed at 204°C. and molded at 232°C. Since compounds (A), (B), (C) and (D) lose at least 10% of their weight before the molding temperature of polypropylene, these materials cannot be used effectively as flame retardants for polypropylene. In contrast, compounds (E) and (G) possess excellent thermal stability and are effective flame retardants for polypropylene as the following Example 11 indicates.

EXAMPLE 11

The flame retardant and Pro-fax 6823 polypropylene base resin was compounded using a C. W. Brabender Prep-Center fitted with a high shear compounding mixer. (Pro-fax 6823 is a trade mark of Hercules Incorporated, 910 Market St., Wilmington, Del. 19899.) The flame retardant additive was dry blended with the polypropylene. Since the capacity of the mixing bowl was only 300 grams, a dip technique for compounding was utilized which consisted of fluxing 300 grams of the dry blend mixture and the removal of approximately 200 grams of the fluxed mixture followed by the addition of more of the dry blend mixture until the total dry blend had been compounded. Each charge was compounded under the same conditions: 400°F. temperature, 120 rmp, with 2 to 3 minute compounding time.

Each flame retarded system was then let down to the desired level by dry blending the ground concentrate and the base resin. The base resin and flame retarded systems were injection molded using a Newbury 30 Ton Injection Molding machine. The following is a set of standard injection molding conditions by which all of the systems were injection molded:

| Rear Zone | 410°F. |
| Front Zone | 440°F. |
| Nozzle | 60°F. |
| Injection Speed | 4 to 5 seconds |
| Cycle Time | 60 seconds |
| Mold Temperature | ~30°C. |
| Flow Mold Time | 1 to 2 seconds |

The above prepared resins were subjected to various tests and the data derived from said tests are reported in Table IV, infra.

TABLE IV

| Flame Retardant Testing in pro-fax 6823 Polypropylene | | | |
|---|---|---|---|
| Flame Retardant | Level F.R. (phr) | O.I.[2] | UL-94[1] |
| None | — | 17.0 | HB |
| E | 12.5 | 25.5 | V-O |
| E | 15.0 | 23.5 | V-O |
| G | 9.0 | 26.5 | V-O |
| G | 12.5 | 27.5 | V-O |
| G | 18.0 | 24.0 | V-O |

[1]UL-94 Flammability Test at a specimen thickness of ⅛ inch, Underwriters' Laboratories, Inc.
[2]Oxygen Index, ASTM D-2863-70.

The difference in thermal stability is not obvious and is the difference between a material which can be used effectively, as the above Example 11 clearly demonstrates, and one which cannot be effectively used because of poor thermal stability in molding and other processing procedures requiring the exposure of said material to elevated temperatures.

Based on this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. A compound of the formula

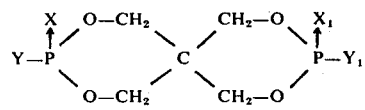

where X and $X_1$ are each oxygen or sulfur and Y and $Y_1$ are each

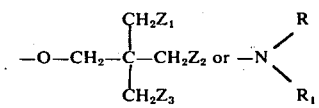

where $Z_1$ and $Z_2$ are independently selected from fluorine, chlorine, bromine, iodine, and hydrogen and wherein $Z_3$ is selected from fluorine, chlorine, bromine, and iodine and where R and $R_1$ are each aliphatic, halogenated aliphatic, aromatic or halogenated aromatic hydrocarbon groups containing not more than about 12 carbon atoms, said halogenated groups having up to about 6 halogen substituents per group.

2. A compound according to claim 1 wherein X and $X_1$ are both oxygen.

3. A compound according to claim 1 wherein Y and $Y_1$ are both

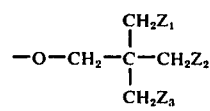

wherein $Z_1$, $Z_2$, and $Z_3$ are independently selected from fluorine, chlorine, bromine, and chlorine.

4. A compound according to claim 3 wherein $Z_1$, $Z_2$, and $Z_3$ are independently selected from chlorine and bromine.

5. A compound according to claim 1 wherein said compound is 3,9-bis(2,2-[dibromomethyl]-3-chloropropoxy)-2,4,8,10-tetraoxa-3,9-diphosphaspiro[5.5]undecane-3,9-dioxide.

6. A compound according to claim 1 wherein Y and $Y_1$ are

7. A compound according to claim 6 wherein the halogen substituents on said R and $R_1$ groups are chlorine, bromine or combinations thereof.

8. A compound according to claim 6 wherein X and $X_1$ are both oxygen.

9. A compound according to claim 8 wherein said R and $R_1$ are phenyl or halogenated phenyl or alkyl or halogenated alkyl having up to about six carbon atoms.

10. A compound according to claim 8 wherein the halogen substituents on said R and $R_1$ groups are chlorine, bromine or combinations thereof.

11. A compound according to claim 8 wherein said R and $R_1$ are phenyl or halogenated phenyl or alkyl or halogenated alkyl having up to about six carbon atoms and from zero to about three halogen substituents.

12. A compound according to claim 6 wherein said R and $R_1$ are phenyl or halogenated phenyl or alkyl or halogenated alkyl having up to about six carbon atoms.

13. A compound according to claim 6 wherein said R and $R_1$ are phenyl or halogenated phenyl or alkyl or halogenated alkyl having up to about six carbon atoms and from zero to about three halogen substituents.

14. A compound according to claim 1 wherein said compound is 3,9-bis(N,N-diethylamino)-2,4,8,10-tetraoxa-3-9-diphosphaspiro[5.5]undecane-3,9-dioxide.

15. A compound according to claim 1 wherein said compound is 3,9-bis(N,N-dimethylamino)-2,4,8,10-tetraoxa-3,9-diphosphaspiro[5.5]undecane-3,9-dioxide.

16. A compound according to claim 1 wherein said compound is 3,9-bis(N-p-bromophenylamino)-2,4,8,10-tetraoxa-3,9-diphosphaspiro[5.5]undecane-3,9-dioxide.

17. A compound according to claim 1 wherein Y and $Y_1$ are both

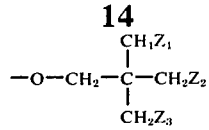

wherein $Z_1$ and $Z_2$ are independently selected from fluorine, chlorine, bromine, iodine, and hydrogen and wherein $Z_3$ is selected from fluorine, chlorine, bromine, and iodine.

18. A compound according to claim 17 wherein said compound is 3,9-bis(2,2-[dibromomethyl]-3-bromopropoxy)-2,4,8,10-tetraoxa-3,9-diphosphaspiro[5.5]undecane-3,9-dioxide.

19. A compound according to claim 17 wherein said compound is 3,9-bis(2,2-[dichloromethyl]-3-chloropropoxy)-2,4,8,10-tetraoxa-3,9-diphosphaspiro[5.5]undecane-3,9-dioxide.

20. A compound according to claim 17 wherein said compound is 3,9-bis(2,2-[dimethyl]-3-chloropropoxy)-2,4,8,10-tetraoxa-3,9-diphosphaspiro[5.5]undecane-3,9-dioxide.

21. A compound according to claim 17 wherein said compound is 3,9-bis(2,2-[dimethyl]-3-bromopropoxy)-2,4,8,10-tetraoxa-3,9-diphosphaspiro[5.5]undecane-3,9-dioxide.

22. A compound of the formula

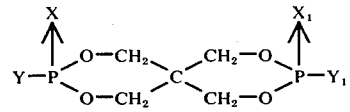

where X and $X_1$ are each oxygen or sulfur and Y and $Y_1$ are each

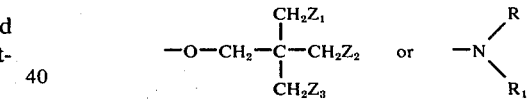

where $Z_1$ and $Z_2$ are independently selected from fluorine, chlorine, bromine, iodine, and hydrogen and wherein $Z_3$ is selected from fluorine, chlorine, bromine, and iodine and where R and $R_1$ are each hydrogen, aliphatic halogenated aliphatic, aromatic or halogenated aromatic hydrocarbon groups containing not more than about 12 carbon atoms, said halogenated groups having up to about 6 halogen substituents per group, and provided that when R and $R_1$ are both hydrogen and X and $X_1$ are both oxygen Y must be different from $Y_1$.

* * * * *

UNITED STATES PATENT OFFICE
CERTIFICATE OF CORRECTION

PATENT NO. : 3,978,167
DATED : August 31, 1976
INVENTOR(S) : James A. Albright

It is certified that error appears in the above-identified patent and that said Letters Patent are hereby corrected as shown below:

Complete Table II at Column 9 by adding on the line following that for Compound C, the Compound D and associated data in same columnar arrangement, namely:

D        9.45        399

Signed and Sealed this

Second Day of November 1976

[SEAL]

Attest:

RUTH C. MASON
Attesting Officer

C. MARSHALL DANN
Commissioner of Patents and Trademarks